United States Patent
Hernandez

(10) Patent No.: US 11,433,006 B2
(45) Date of Patent: Sep. 6, 2022

(54) METHODS, COMPOSITIONS, AND DELIVERY SYSTEMS FOR THERAPEUTIC SKIN TREATMENTS

(71) Applicant: Topix Pharmaceuticals, Inc., North Amityville, NY (US)

(72) Inventor: Steven M. Hernandez, Blue Point, NY (US)

(73) Assignee: Topix Pharmaceuticals, Inc., North Amityville, NY (US)

( * ) Notice: Subject to any disclaimer, the term of this patent is extended or adjusted under 35 U.S.C. 154(b) by 0 days.

(21) Appl. No.: 16/800,015

(22) Filed: Feb. 25, 2020

(65) Prior Publication Data

US 2020/0268618 A1 Aug. 27, 2020

Related U.S. Application Data

(60) Provisional application No. 62/810,079, filed on Feb. 25, 2019.

(51) Int. Cl.
| | | |
|---|---|---|
| *A61K 8/02* | (2006.01) | |
| *A61K 8/64* | (2006.01) | |
| *A61K 8/73* | (2006.01) | |
| *A61K 8/9789* | (2017.01) | |
| *A61K 8/34* | (2006.01) | |
| *A61K 8/49* | (2006.01) | |
| *A61Q 19/08* | (2006.01) | |
| *A61Q 19/00* | (2006.01) | |
| *A61B 17/3209* | (2006.01) | |
| *A61B 17/00* | (2006.01) | |

(52) U.S. Cl.
CPC ...... *A61K 8/0212* (2013.01); *A61B 17/32093* (2013.01); *A61K 8/347* (2013.01); *A61K 8/4946* (2013.01); *A61K 8/4953* (2013.01); *A61K 8/64* (2013.01); *A61K 8/731* (2013.01); *A61K 8/735* (2013.01); *A61K 8/9789* (2017.08); *A61Q 19/007* (2013.01); *A61Q 19/08* (2013.01); *A61B 2017/00747* (2013.01)

(58) Field of Classification Search
CPC ........ A61K 8/0212; A61K 8/64; A61K 8/731; A61K 8/9789; A61K 8/347; A61K 8/4946; A61K 8/735; A61K 8/4953; A61Q 19/08; A61Q 19/007; A61B 17/32093; A61B 2017/00747
See application file for complete search history.

(56) References Cited

U.S. PATENT DOCUMENTS

| | | | |
|---|---|---|---|
| 7,314,634 B2 * | 1/2008 | Hernandez | A61Q 19/00 424/401 |
| 7,902,329 B2 * | 3/2011 | Hantash | A61P 17/16 530/326 |
| 7,977,290 B1 * | 7/2011 | Deane | A61Q 19/10 510/130 |
| 9,226,886 B2 | 1/2016 | Lee et al. | |
| 9,820,953 B2 * | 11/2017 | Black | A61K 31/194 |
| 2007/0065396 A1 | 3/2007 | Marius et al. | |
| 2014/0228291 A1 * | 8/2014 | Saxena | A61K 8/585 514/8.9 |
| 2014/0364365 A1 | 12/2014 | Wu et al. | |
| 2017/0333299 A1 | 11/2017 | Lin et al. | |
| 2018/0092355 A1 | 4/2018 | Kim et al. | |

FOREIGN PATENT DOCUMENTS

| | | | | |
|---|---|---|---|---|
| CN | 105496828 A | 4/2016 | | |
| CN | 105496868 A | 4/2016 | | |
| CN | 108403469 A | 4/2016 | | |
| CN | 107106549 A | 8/2017 | | |
| WO | 2012131623 A2 | 10/2012 | | |
| WO | WO-2012131623 A2 * | 10/2012 | | A61K 8/365 |
| WO | 2016029021 A1 | 2/2016 | | |

OTHER PUBLICATIONS

"Biocellulose Restorative Mask" Retrieved from the Internet Aug. 31, 2018, URL: https://www.skinceuticals.com/biocellulose-restorative-mask-3606000497573.html.
International Search Report for PCT/US2020/019579 dated Jun. 22, 2020, 2 pages.
Office Action with English Translation for Chinese Patent Application No. 202080016610.4 dated May 23, 2022, 12 pages.

* cited by examiner

*Primary Examiner* — Robert A Wax
*Assistant Examiner* — William Craigo
(74) *Attorney, Agent, or Firm* — Lowenstein Sandler LLP

(57) ABSTRACT

Disclosed are skincare formulations, delivery systems and treatment methods containing an oligopeptide and a combination of antioxidants for topical application to the skin before and/or after dermatological procedures that affect the skin's barrier. The systems herein alleviate discomfort and enable rapid healing of irritated and damaged skin, and provide improved treatment outcomes for dermatological procedures. The disclosed topical formulations, delivery systems, and methods thereof provide enhanced penetration of the active ingredients to the skin while maintaining skin moisture and protecting sensitive skin after dermatological procedures for improvement of aesthetic skin properties. Also provided are methods for therapeutic treatment of dermatological conditions by topically applying, using, for example, a pre-moistened bio-cellulose mask, a formulation comprising (% w/w) at least 0.0001% palmitoyl sh-tripeptide-4 amide on an active basis and at least 0.1% *Camellia sinensis* leaf extract.

7 Claims, No Drawings

METHODS, COMPOSITIONS, AND DELIVERY SYSTEMS FOR THERAPEUTIC SKIN TREATMENTS

CROSS-REFERENCE TO RELATED APPLICATIONS

This application claims the benefit under 35 U.S.C. § 119(e) to U.S. Provisional Patent Application Ser. No. 62/810,079, filed Feb. 25, 2019, the entire contents of which are incorporated herein by reference.

FIELD

The present invention relates to the field of therapeutic treatments and compositions for skincare, including skincare treatments and formulations for application to the skin, for example, in combination with any skincare treatment or regimen at-home or professionally administered, including before and/or after dermatological procedures that affect, for example, disrupt, the skin's barrier to alleviate discomfort and enable healing of the skin and to improve treatment outcomes, as well as to methods for their application to the skin, formulation, manufacture and use thereof.

BACKGROUND

Various dermatological procedures, such as microneedling, RF microneedling, laser, chemical peels, intense light therapy, microdermabrasion or dermaplaning, are used to treat and improve conditions like acne scarring, fine lines and wrinkles, loose skin, skin texture, pore size, brown spots, stretch marks, and pigment issues. Such procedures tend to disrupt the skin's barrier and/or cause redness, irritation, inflammation, among other skin conditions, which need to be addressed and corrected. For example, in microneedling procedures the microneedling depth is enough to draw blood and to irritate and/or inflame the skin, which could require healing.

Other anti-aging and corrective skin procedures can involve chemical, thermal and mechanical wounds. Patients having such treatments have extremely irritated and sensitive skin after the treatment requiring further post-procedure treatments with, for example, cold compresses, wet soaks or occlusive ointments. However, some such post-treatments may cause further irritation and inflammation, rather than alleviate the post-procedure condition being treated.

Mask sheets are used in skincare and are shaped to be attached to, for example, the face. Such masks are used for burn treatment, skin moisturizing, skin whitening or skin nutrition, and are made of non-woven fabrics, such as vegetable cellulose fibers, i.e., cotton or pulp, or of synthetic fibers. Some such sheets have been found problematic since the sheets dry within a short period of time after application and foreign materials, such as dust, may also get attached to the skin along with the mask sheets. Bio-cellulose mask sheets saturated with water also are used for applying to the skin.

The prior methods, formulations, and delivery systems, however, do not provide efficacious and fast acting pain and swelling relief, or improved treatment outcomes from the applied dermatological procedures. Typically, such do not prevent discomfort and inflammation, and are not effective in rapid healing of the skin conditions described above that occur, for example, in situations of dermatological procedures affecting the skin's barrier.

Accordingly, there is a need in the art for improved methods, formulations and delivery systems thereof that can provide treatment to the skin of those in need thereof to alleviate and ameliorate one or more of the conditions noted above. More specifically, there is a need in the art for improved skincare formulations and methods to treat redness, irritation, inflammation, among other skin conditions, and to improve treatment outcomes in dermatological office procedures, by utilizing such formulations and methods either before or after dermatological procedures, such as microneedling, laser, chemical peels, intense light therapy, microdermabrasion or dermaplaning, that cause disruption, irritation and/or inflammation of the skin, and with other anti-aging and corrective skin procedures that can involve chemical, thermal and mechanical irritation and wounds to the skin.

The methods and systems disclosed herein are designed to provide cooling and soothing features to sooth, calm, reduce redness, swelling and burning sensations, and prevent inflammation and promote healing more effectively than prior topical formulations and systems.

SUMMARY

The present disclosure provides skincare treatments, formulations, and delivery systems thereof, and more particularly, therapeutic treatments and delivery systems with formulations having a therapeutically effective amount of an oligopeptide and one or more antioxidants.

In certain embodiments, the oligopeptide is at least 0.001% w/w on an active basis. In other embodiments, the one or more antioxidant is at least 0.1% w/w. The disclosed embodiments, treat redness, swelling, burning, and other such dermatological conditions.

Aspects of the present disclosure provide methods for therapeutic treatment of skin in dermatological procedures by topically applying to skin, selected for a dermatological procedure, a therapeutically effective amount of a formulation comprising an oligopeptide and one or more antioxidants, wherein the oligopeptide is at least 0.0001% w/w on an active basis and the one or more antioxidant is at least 0.1% w/w. In certain embodiments, the dermatological procedure affects the skin's barrier. The dermatological procedures may include microneedling, RF microneedling, laser, chemical peels, intense light therapy, microdermabrasion, dermaplaning.

In aspects of the present disclosure, the methods include applying a microneedling procedure to the skin, topically applying the formulation before the microneedling procedure, and topically applying the formulation after the microneedling procedure.

The formulation is effective in one or more of healing, reducing symptoms associated with dermatological procedures, soothing the skin, enhancing treatment outcome. The methods disclosed herein may include applying a biocellulose mask to the skin selected for a dermatological procedure, wherein the biocellulose mask is pre-moistened with the formulation.

In further aspects of the present disclosure, the oligopeptide is palmitoyl sh-tripeptide-4 amide. In yet further aspects of the present disclosure, the antioxidant is one or more of *Camellia sinensis* leaf extract, resveratrol, ectoin, *Cucumis satvius* fruit extract, ergothioneine, *Phyllanthus emblica* fruit extract.

In aspects disclosed herein, the skin may be very dry human skin. In yet further aspects, the formulation may include one or more of purified water, hydrolyzed sodium hyaluronate, sodium hyaluronate, *Camellia sinensis* leaf extract, resveratrol, palmitoyl sh-tripeptide-4 amide, ectoin, bisabolol, *Cucumis satvius* fruit extract, ergothioneine, *Phyllanthus emblica* fruit extract, caffeine. In yet further aspects of the present disclosure, the formulation is sterile.

The present disclosure contemplates the dermatological procedure is an at-home skin practice or regimen. The present disclosure further contemplates, the dermatological procedure is a cosmetic procedure performed by a physician, esthetician, skincare practitioner, or home user.

Aspects of the present disclosure include a topical formulation for therapeutic treatment of skin in dermatological procedures, comprising an oligopeptide and one or more antioxidants, wherein the oligopeptide is at least 0.0001% w/w on an active basis and the one or more antioxidant is at least 0.1% w/w.

In aspects herein, the formulation includes (% w/w) 10%-99% purified water; 0.001%-75% hydrolyzed sodium hyaluronate; 0.001%-10% sodium hyaluronate; 0.001%-99% *Camellia sinensis* leaf extract; 0.001%-5.0% resveratrol; 0.0001%-1% palmitoyl sh-tripeptide-4 amide; 0.001%-5% ectoin; 0.001%-5% ergothioneine; 0.001%-5% bisabolol; 0.001%-99% *Cucumis satvius* fruit extract; 0.001%-99% sodium pyrrolidone carboxylic acid (PCA); 0.001%-99% *Chamomila recutita* flower extract; 0.001%-99% comfrey extract (e.g., ABS comfrey extract paraben free (PF)); 0.001%-99% *yucca glauca* root extract; 0.001%-5% *Phyllanthus emblica* fruit extract; 0.001%-5% caffeine; 0%-2% sodium phosphate; 0%-0.5% potassium hydroxide; 0.0%-3.5% phenylcarbinol; 0.0%-0.5% sodium benzoate; 0.0%-0.3% disodium Ethylenediaminetetraacetic acid (EDTA); 0.01%-10% polysorbate 20.

In yet further aspects of the present disclosure, the formulation includes (% w/w) 82.41% purified water; 1.00% hydrolyzed sodium hyaluronate; 0.10% sodium hyaluronate; 0.01% *Camellia sinensis* leaf extract; 0.01% resveratrol; 4.00% palmitoyl sh-tripeptide-4 amide; 0.01% ectoin; 0.01% ergothioneine; 0.20% bisabolol; 0.01% *Cucumis satvius* fruit extract; 0.01% sodium PCA; 0.01% *Chamomila recutita* flower extract; 0.01% ABS comfrey extract PF (*Symphytum officinale* leaf extract, *Leuconostoc*/radish root ferment filtrate); 0.01% *yucca glauca* root extract; 0.10% *Phyllanthus emblica* fruit extract; 0.01% caffeine; 0.638% sodium phosphate; 0.226% potassium hydroxide; 0.20% phenylcarbinol; 0.05% sodium benzoate; 0.05% disodium EDTA; 0.70% polysorbate 20.

Aspects of the present disclosure provide a sheet for therapeutic treatment of skin in dermatological procedures, comprising the sheet structured for topical application to skin selected for a dermatological procedure, the sheet being pre-moistened with a therapeutically effective amount of a formulation comprising an oligopeptide and one or more antioxidants, wherein the oligopeptide is at least 0.0001% w/w on an active basis and the one or more antioxidant is at least 0.1% w/w. In aspects herein, the sheet may be a biocellulose sheet structured as a facial mask. In yet other aspects of the present disclosure, the formulation and/or sheet pre-moistened with the formulation is sterilized.

The compositions and delivery systems exhibit low irritancy, and improved, synergistic efficiency of the formulated ingredients, including improved alleviation of discomfort and healing in the subject. In particular, the present disclosure provides cosmetic treatments and delivery systems with formulations having a combination of components, which exhibit lower irritancy, better regression time, and improved penetration properties of all the formulated active ingredients into the skin as compared with other skincare products.

The present disclosure contemplates use of the disclosed formulations as pre-treatment and/or post-treatment agents for skincare treatments. As discussed in further detail below, the formulations of the present disclosure have enhanced discomfort relief and provide enhanced healing of the skin in conditions arising from certain dermatological procedures.

More specifically, the present disclosure contemplates use of the methods of treatment and formulations herein both in pre-treatment and post-treatment modes. In pre-treatment, the skin is conditioned, cooling and hydrating it as well as transdermally delivering or topically providing antioxidants, peptides, humectants, and soothing botanicals, preventing or reducing negative effects of the procedure, skincare regimen or other skin disruptive or other barrier disruptive aggressors, such as sun exposure, dry climate, intrinsic and extrinsic skin dryness, redness, irritation, swelling, and wounds.

In post-treatment, the methods of treatment and formulations herein work to prevent and decrease both immediate and late onset of undesirable effects, such as redness, swelling, edema, itching, burning, wounds of the skin, bleeding, sensitive skin, skin damage, post-procedure hyperpigmentation, scabbing, and weeping wounds. As a result, the methods of treatment and formulations herein also improve treatment outcomes and aid in patient compliance with their post-procedure care. The methods of treatment and formulations herein also make it possible to have the procedures, when administered as a series over time, repeated at closer intervals due to faster recovery. Aside from alleviating discomfort and raw or challenged skin appearance post-procedure, use of the methods of treatment and formulations herein allow the user to return to normal activities faster, and with less discomfort or side effects.

Topical application of the disclosed formulations may include application to specific body areas, such as, without limitation, feet, elbows, knees, that are susceptible to dermatological conditions of the type requiring the therapeutic treatments disclosed herein. Such treatments may be applied, for example, 1-3 times per day, for example, after showering, among others. The present disclosure contemplates that the disclosed treatments would reduce the dermatological conditions of the affected areas, followed by regular topical applications, as desirable or necessary, to maintain the improved condition of the body areas under treatment.

In some embodiments, the present disclosure provides formulations comprising sodium hyaluronate, such as hydrolyzed sodium hyaluronate. The present disclosure contemplates other combinations of the active ingredients disclosed herein such that the desired improved treatment results are achieved. Surprisingly, it has been found that the combination of a peptide, such as, palmitoyl sh-tripeptide amide, and antioxidants, such as *Camellia sinensis* leaf extract, or hydrolyzed sodium hyaluronate or green tea polyphenols or ectoin or ergothioneine or emblica or bisabolol or resveratrol or other antioxidants, either alone, but advantageously in combination, and most advantageously in the combinations listed herein, yields surprising and unexpected results for healing and irritation relief in skincare procedures.

The disclosed treatments comprise one or more peptides, antioxidants, sodium hyaluronate, including hydrolyzed sodium hyaluronate.

The disclosed compositions may also comprise one or more moisturizers and/or humectants. In one aspect of this embodiment, the moisturizer and/or humectant is sodium hyaluronate, such as fractionated and long-chain sodium hyaluronate, from single monomer to about 5 million Daltons, to bind moisture to the skin and penetrate the skin carrying moisture.

The disclosed formulations may also comprise skin soothing agents, such as antioxidants, to reduce skin inflammation and irritation.

The disclosed treatments may also comprise one or more soothing antioxidants to calm the skin and reduce inflammation. In one aspect of this embodiment, the antioxidant is a polyphenol. In a more specific aspect of this embodiment, the antioxidant comprises a polyphenol isolate, or a mixture of polyphenol isolates, of *Camellia sinensis*.

In certain embodiments, the disclosed treatments may be provided using a sheet-like structure, such as a face mask configured for attachment to an area selected for a dermatological procedure. The present inventors have found biocellulose face masks surprisingly effective in providing the therapeutic treatments with the disclosed formulations, as discussed in further detail hereinafter.

DETAILED DESCRIPTION

The present disclosure provides skincare formulations, delivery systems, and methods of use thereof for alleviation or amelioration of dermatological conditions relating to dermatological procedures that irritate and/or wound human skin. Dermatological conditions amenable to treatments disclosed herein include, without limitation, inflammatory disorders of the skin and skin conditions characterized by increased cell turnover including psoriasis, photoaging, weather-beaten appearance, yellowing, loss of elasticity, loss of collagen rich appearance and/or youthfulness, redness, dryness, age spots, skin wrinkles, acne, rosacea, ichthyosis. The disclosed therapeutic formulations are also useful for improvement in one or more aesthetic criteria, including, but not limited to, a perceived improvement in apparent skin age, skin tone, weather-beaten appearance, yellowing, loss of elasticity, redness, dryness, age spots, skin wrinkles, skin smoothness, brightness, radiance, as well as skin pores becoming less noticeable.

As used herein, the terms "treatment" or "treating" with respect to a skin condition generally mean "having positive effect on a skin condition" and encompass reduction, amelioration, and/or alleviation of at least one symptom of a skin condition, a reduction, amelioration, and/or alleviation in the severity of the skin conditions, or delay, prevention, or inhibition of the progression of the skin condition. Treatment, as used herein, therefore does not require total curing of the condition. A formulation of the present disclosure that is useful for treatment of a skin condition, or a method of treating a skin condition, need only reduce the severity of a skin condition, reduce the severity of symptoms associated therewith, provide improvement to a patient's quality of life, or delay, prevent, or inhibit the onset of one or more symptoms of a skin condition. As used herein, these terms also encompass aesthetic improvements to the skin upon application of the disclosed formulations having a combination of, for example, an oligopeptide, antioxidants, and hyaluronic acid or its derivatives.

As used herein, the terms "application," "apply," and "applying" with respect to a disclosed topical formulation or method of using a disclosed topical formulation, refer to any manner of administering a topical formulation to the skin of a patient which, in medical or cosmetology practice, delivers the formulation to the patient's skin surface. Smearing, rubbing, spreading, spraying a disclosed topical formulation, with or without the aid of suitable devices, on a patient's skin are all included within the scope of the term "application," as used herein. The term "topical" or "topically" with respect to administration or application of a disclosed skincare formulation refers to epicutaneous administration or application, onto skin.

The present disclosure further contemplates administration or application of the disclosed skincare formulations using a sheet-like structure, such as a mask configured for attachment to a desired area. In particular, the present disclosure contemplates use of applicator systems, such as biocellulose face masks, which are surprisingly effective in providing therapeutic treatments with the disclosed formulations.

A biocellulose mask is a device, generally supplied as a sheet, either individual or multiple quantities per package, which may be pre-cut to conform more easily to a particular body area or, for example, contain cut-out areas for eyes, nose, mouth, or perhaps have cuts or wedges removed in order to facilitate better adhesion to the skin when wet with water or a treatment solution.

The present disclosure contemplates any suitable biocellulose material for the types of masks disclosed herein. In this, a person skilled in the art would be familiar with such materials and masks thereof. Biocellulose fibers are hydrophilic and hold water and hydrophilic solutions very efficiently. They conform well to the skin providing an efficient diffusion gradient, with beneficial ingredients entering the skin and having the potential to absorb unwanted allergens or chemicals from the skin. The moisture trapping ability allows the mask to evaporate water at a high rate, causing continued cooling over long periods of time, even when applied to warm skin. This provides cooling comfort and reduction of redness, swelling and other complications after laser or other treatments which may disrupt the skin's barrier, via physical, thermal, chemical or other types of wounding. Further, this provides effective treatment and healing of such types of skin barrier wounding.

Biocellulose fibers and sheet goods may be easily sterilized by heat, chemical, radiation, or other methods. They are largely inert and do not irritate or exacerbate skin injury during treatment. They transmit active ingredients efficiently and hold them in stable formulation over a reasonable shelf life.

The present disclosure further contemplates the use of masks of any substrate material that is suitable for the purposes and results discussed herein.

As used herein, the phrase "effective amount" refers to an amount of a formulation of the present disclosure, or component thereof, effective to treat a skin condition as noted above, including a range of effects, from a detectable local improvement in an area of topical application to substantial relief of symptoms to an improvement in one or more aesthetic criteria, including, but not limited to, a perceived improvement in apparent skin dryness, keratosis pilaris, age, radiation damage, sun or uv damage, skin tone, weather-beaten appearance, yellowing, loss of elasticity, redness, dryness, age spots, skin wrinkles, skin smoothness, brightness, radiance, as well as skin pores becoming less noticeable. The effective amount will vary with the particular condition or conditions being treated, the severity of the condition, the duration of the treatment, the specific components of the composition being used, and other factors. More specifically, the disclosed compositions and formulations provide a method for therapeutic treatment of skin by providing, in some embodiments, a combination of an oligopeptide and an antioxidant, in an efficacious manner to the skin.

The disclosed compositions, formulations and methods of use thereof reduce, minimize, or eliminate normally-observed dry skin conditions including, *inter alia*, conditions characterized by redness, swelling, itching, severe skin flaking, breakdown of the skin barrier, discomfort, extreme dryness, cracking of the skin, burning sensation and sensitization. The disclosed compositions, formulations, and methods of use thereof also provide aesthetic improvements in the skin, including, but not limited to, skin that appears younger, skin exhibiting a more even tone, skin in which the pores are less noticeable, and skin that is judged by the user to be smoother, and/or to be improved with respect to its weather-beaten or aged appearance, yellowing, loss of elasticity, redness, dryness, age spots, and/or skin wrinkles and scarring, for example, acne scarring and other pitted lesions and melasma or other skin pigmentation issues immediately after medical or aesthetic procedures to the skin and for a length of time thereafter where the subject may feel discomfort or dryness of any kind.

As used herein, the phrase "skin barrier" refers to the outermost layer of the skin's surface. As is generally known, the skin barrier has cells and lipids, and may also be referred to as the permeability barrier, moisture barrier, or lipid barrier. The skin barrier prevents evaporation of essential water and electrolytes from the skin, among other functions. As disclosed herein, various processes may disrupt, i.e., weaken or affect, the skin barrier causing, among others, pain, swelling, redness, dryness, irritation, susceptibility to infection, which require healing and repair. The extent of skin barrier disruption may vary based on the specific dermatological procedure from minor penetration to depths that draw blood to the skin surface. For example, microneedling procedures may be adjusted for depths of penetration based on the skin conditions under treatment. Various dermatological procedures are used for promoting collagen production to treat skin conditions.

As used herein, the phrase "dermatological procedure" refers to surgical, medical, or simple procedures, for example, rendered by a physician, esthetician, skincare service provider, or end-user at home. For example, at home daily, simple cleansing and moisturizing routines, such as treating a person's simple dry skin condition, affecting the skin barrier, are within the scope of the phrase "dermatological procedure."

As used herein, the terms "masks" or "mask sheets" refer to shaped or unshaped sheet-like structures that are used in skincare and may be shaped to be attached to, for example, the face. Such sheets are used for burn treatment, skin moisturizing, skin whitening or skin nutrition, and are made of non-woven fabrics, such as vegetable cellulose fibers, i.e., cotton or pulp, or of synthetic fibers. In certain embodiments herein, biocellulose sheets saturated with formulations disclosed herein may be used for effectively delivering active agents to the skin and for protecting and soothing the skin barrier.

As used herein, the term "on an active basis" refers to the actual percentage or composition of an active ingredient, such as a peptide, as used in a formulation.

Sheets may be used, for example, for facial masks, adhesive skin patches, or the like, used for facial treatment, skin treatment, or the like, including delivery systems, i.e., carriers, of active ingredients such as skin healing/repair components, and the like. These sheets are adhered to the skin to impart active components contained in the sheets to the skin surface. In addition, when a sheet contains various active ingredients and is tightly adhered to the skin, the sheet provides functions, such as controlling skin temperature, water retention and/or supplying the active ingredients in the sheet to the skin. In particular, when a sheet having a liquid component is adhered to the skin and kept in place for some time, physiology of the skin can be improved owing to, for example, favorable moisture content or temperature. Such functionality of the systems disclosed herein have surprisingly been found to improve penetration of active agents into the skin thereby enabling rapid healing and relief from irritation and redness.

In addition to the foregoing, the present disclosure contemplates use of additional methods of applying the disclosed formulations including, but not limited to, spray aerosol, cotton pads and balls, gauze, foam, tissue applicators, human hands, among others.

The skincare compositions and delivery systems disclosed herein not only maintain the active properties of the active agents, but also provide greater efficiency of the active agents. In one aspect of this disclosure the skin is human skin. In other aspects of the present disclosure, the skin is that of a companion animal, a domestic animal, or a commercially useful animal.

The present inventors have found that the treatments of the present disclosure are effective therapeutically for treating dermatological conditions. In certain embodiments of the present disclosure, skincare formulations are provided having 0.01% of palmitoyl sh-tripeptide 4 amide, 0.2% of an antioxidant, 1% of sodium hyaluronate, such as hydrolyzed sodium hyaluronate.

In certain embodiments, the disclosed compositions may also comprise one or more moisturizers and/or humectants.

Humectants are hygroscopic substances used to keep things moist, often a molecule with several hydrophilic groups, or capable of hydrogen bonding with water, or having other polar organic functional groups. Humectants can also function as solvents or cosolvents.

Some examples of humectants include, but are not limited to, amino acids; glycols and polyols, such as propylene glycol, hexylene glycol, and butylene glycol, including polymeric and sugar-based polyols/alcohols, for example, glycerol, sorbitol, xylitol, maltitol, polydextrose; mucopolysaccharides and carbohydrates, for example, aloe vera gel, yucca extract, dextrose and polydextrose; alpha hydroxy acids such as glycolic acid, lactic acid; albumen; esters or amides of acetic acid or similar; soluble carbohydrates, such as sugar, honey; salts, such as potassium chloride, sodium PCA, salts of polycarboxylic acids; amides, such as urea and urea derivatives.

In one aspect of these embodiments, the moisturizer and/or humectant is sodium hyaluronate, such as fractionated and long-chain sodium hyaluronate, from single monomer to about 5 million Daltons, to bind moisture to the skin and penetrate the skin carrying moisture. Hyaluronate is a moisture binder that helps keep the skin hydrated and provides "slip" (sensory aesthetics) to the disclosed formulations.

The disclosed formulations also comprise one or more solubilizing agents, rheology modifiers and/or emulsifiers. In one aspect of this embodiment, the solubilizing agent/emulsifier is a non-ionic solubilizing agent/emulsifier. In one specific aspect of this embodiment, the solubilizing agent/emulsifier is polysorbate 20.

In other aspects of these embodiments, the emulsifier may be one or more of PEG-100 stearate. cetearyl alcohol, cetearyl glucoside, polysorbate 60, stearyl alcohol, glyceryl stearate, sodium polyacrylate, emulsifying wax.

In further aspects of the disclosed formulations, xanthan gum, such as Keltrol T®, may be provided as an emulsifier for a stable emulsion.

In yet further aspects of the disclosed formulations, an artificial thickening agent, such as Rapithix A-60® from Ashland Chemical, may be provided.

The disclosed treatments may also comprise one or more soothing antioxidants to calm the skin and reduce inflammation.

Antioxidants inhibit oxidation, a type of chemical reaction that may produce free radicals. Antioxidants may assist in modulating inflammation, preventing or diminishing allergic or irritant reactions in the skin, including overstimulation of histamine up-regulation.

In this, in the presently disclosed formulations and treatments antioxidants assist in reducing the sting and irritation normally associated with application of high levels of active ingredients, as well as calming the existing condition for which the skin is being treated. This brings relief to the user, which leads to heightened compliance with the subject's treatment protocols.

Exemplary antioxidants include, but are not limited to, polyphenols, ergothioneine, glutathione, tetrahexyldecyl ascorbate, ascorbate derivatives, tocopherols or derivatives thereof, herbals such as pomegranate, cranberry, quercetin, carotenoids, resveratrol, ferulic acid, caffeic acid, gallic acid, topical compounds preventing or reducing the number of oxidative events in the skin, whether or not induced by uv light or solar exposure.

In one aspect of this embodiment, the antioxidant is a polyphenol. In a more specific aspect of this embodiment, the antioxidant comprises a polyphenol isolate of *Camellia sinensis*. The antioxidant can be a polyphenol or a mixture thereof that is isolated from plants, chemically synthesized; the antioxidant can also be a semi-synthetic compound prepared by modification of a natural polyphenol or mixture of polyphenols. In specific embodiments of the present disclosure, the antioxidant includes "green tea polyphenols" isolated and purified from the leaves of *Camellia sinensis* plants. These antioxidants, as formulated and delivered herein, provide antioxidant activity as well as anti-inflammatory activity, and, further, provide skin soothing, protection, and repair activity.

Other antioxidants contemplated by the present disclosure include, but are not limited to, vitamin E acetate.

The disclosed treatments may also comprise one or more emollients. Emollients soften, lubricate and protect the skin from trans-epidermal water loss (TEWL). Some examples of emollients include, but are not limited to, lipids, phospholipids, occlusives, petrolatum, waxes, paraffinic oils, vegetable and animal fats, esters, such as isopropyl myristate, dicaprylyl carbonate, isopropyl palmitate, ethoxylates or propoxylates esters and fats, silicones, butters (cocoa butter, shea butter, etc.) and polyethylene glycols (PEG).

Skin lipids are the "mortar" in the brick and mortar model of the skin. These fats, oils and waxes may have more or less hydrophilic tendency and help prevent trans-epidermal water loss (TEWL), and allow the skin to retain moisture and more effectively repair itself. Examples are ceramides, phospholipids, phytosphingosine, cholesterol, lanosterol, fatty acids, sebum components, many of which can exist and be functional in its natural form, or be functional in the presently disclosed compositions and treatments as a derivative or synthetic analog.

In one aspect of this embodiment, the emollient is an ester or oil. In various aspects of this embodiment, the emollient can include, without limitation, one or more of the following shea butter, cocoa butter, mineral oil, lanolin, petrolatum, paraffin, beeswax, squalene, squalane, cetyl alcohol, olive oil, triethylhexanoin, coconut oil, jojoba oil, sesame oil, almond oil, or other plant oils, lipids, and combinations of two or more thereof.

Other emollients contemplated by the present disclosure include, but are not limited to, caprylic/capric triglyceride.

The disclosed formulations may also comprise other skin soothing agents, such as antioxidants, to reduce skin inflammation and irritation, and bio-mimetic ceramide complex that mimics the skin's natural lipid profile.

In certain embodiments of the presently disclosed formulations, ingredients therein include amino acid mixtures having one or more amino acids. In specific aspects of these embodiments, the amino acid mixtures have a profile of the human skin's natural moisturizing factor (NMF).

In other embodiments of the present disclosure, the skin treatment formulations include an amino acid mixture, having a profile of the human skin's natural moisturizing factor (NMF), including the following components formulated within the indicated ranges (all expressed as % w/w): Purified water (QS to 100%), disodium EDTA (0.10%), glycine (1.612%), L-citrulline (1.00%), L-alanine (0.921%), L-proline (0.148%), L-ornithine monohydrochloride (0.287%), L-arginine (0.073%), L-glutamic acid (0.243%), L-histidine (0.429%), valine (0.381%), L-lysine (0.179%), L-aspartic Acid (0.30%), leucine (0.262%), threonine (0.713%), tyrosine (0.295%), DL-phenylalanine (0.283%), taurine (0.032%), L-isoleucine (0.194%), methionine (0.072%), serine (2.32%).

In certain embodiments of the present disclosure, the formulations may include one or more solubilizing/emulsifying, skin-conditioning/treating agents and preservatives/stabilizing agents, such as butylene glycol, caprylic/capric triglyceride, phospholipids, SK-Influx V®, glycerin, lecithin, tocopheryl acetate, ubiquinone (co-enzyme Q10), hydrolyzed glycosaminoglycans, hexanoyl dipeptide-3 norleucine acetate, salix nigra (willow) bark extract, mandelic acid, bisabolol, ceramide NP, ceramide AP, phytosphingosine, cholesterol, ceramides EOP, glycine, citrulline, alanine, proline, ornithine HCl, arginine, glutamic acid, histidine, valine, lysine, aspartic acid, leucine, threonine, tyrosine, phenylalanine, taurine, isoleucine, methionine, serine, sodium lauroyl lactylate, hydrogenated polydecene, trideceth-6, xanthan gum, carbomer, sodium benzoate, phenoxyethanol, disodium EDTA.

In one embodiment of the present disclosure, the skin treatment formulations include the following ingredients: purified water, hydrolyzed sodium hyaluronate, sodium hyaluronate, *Camellia sinensis* leaf extract, resveratrol, palmitoyl sh-tripeptide-4 amide, ectoin, ergothioneine, bisabolol, *Cucumis satvius* (cucumber) fruit extract, sodium PCA, *Chamomila recutita* (matricaria) flower extract, ABS comfrey extract PF (*Symphytum officinale* leaf extract, *Leuconostoc*/radish root ferment filtrate), *yucca glauca* root extract, *Phyllanthus emblica* fruit extract, caffeine, sodium phosphate, potassium hydroxide, phenylcarbinol, sodium benzoate, disodium EDTA, polysorbate 20.

In other embodiments of the present disclosure, the skin treatment formulations include the following components formulated within the indicated ranges (all expressed as % w/w): water (10%-99%), hydrolyzed sodium hyaluronate (0.001%-75%), sodium hyaluronate (0.001%-10.0%), *Camellia sinensis* leaf extract (0.001%-99%), resveratrol (0.001%-5.0%), palmitoyl sh-tripeptide-4 amide (0.0001%-4.0% on an active basis), ectoin (0.001%-5.0%), ergothioneine (0.001%-5.0%), bisabolol (0.001%-10%), *Cucumis sat-*

*vius* (cucumber) fruit extract (0.001%-99%), sodium PCA (0.001%-99%), *Chamomila recutita* (matricaria) flower extract (0.001%-99%), ABS comfrey extract PF (*Symphytum officinale*) leaf extract (0.001%-99%), *Leuconostoc*/radish root ferment filtrate (0.0%-5%), *yucca glauca* root extract (0.001%-99%), *Phyllanthus emblica* fruit extract (0.001%-5.0% on an active basis), caffeine (0.001%-5.0%), sodium phosphate (0.0%-2.0%), potassium hydroxide (0.0%-0.5%), phenylcarbinol (0.0%-3.5%), sodium benzoate (0.0%-0.5%), disodium EDTA (0.0%-0.3%), polysorbate 20 (0.0%-10.0%).

In certain embodiments of the present disclosure, the formulation includes the following ingredients formulated within the indicated ranges (all expressed as % w/w): purified water (82.41%), hydrolyzed sodium hyaluronate (1.00%), sodium hyaluronate (0.10%), *Camellia sinensis* leaf extract (0.01%), resveratrol (0.01%), palmitoyl sh-tripeptide-4 amide (4.00%), ectoin (0.01%), ergothioneine (0.01%), bisabolol (0.20%), *Cucumis Satvius* (cucumber) fruit extract (0.01%), sodium PCA (0.01%), *Chamomila recutita* (matricaria) flower extract (0.01%), ABS comfrey extract PF (*Symphytum officinale*) leaf extract, *Leuconostoc*/radish root ferment filtrate (0.01%), *yucca glauca* root extract (0.01%), *Phyllanthus emblica* fruit extract (0.10%), caffeine (0.01%), sodium phosphate (0.638%), potassium hydroxide (0.226%), phenylcarbinol (0.20%), sodium benzoate (0.05%), disodium EDTA (0.05%), polysorbate 20 (0.70%).

Topical application of the disclosed formulations may include application to specific body areas, such as, without limitation, feet, elbows, knees, that are susceptible to dermatological conditions of the type requiring the therapeutic treatments disclosed herein. Such treatments may be applied, for example, 1-3 times per day, for example, before and/after invasive dermatological procedures of affected areas, followed by regular topical applications, as desirable or necessary, to maintain the improved condition of the body areas under treatment. In certain embodiments, the actual dosage of the formulations of the present disclosure to be topically applied to the skin will depend on, *inter alia*, the condition to be treated, the particular regimen to be followed, and the persona preferences of the user.

The present disclosure contemplates the use of masks or mask sheets, shaped or unshaped, as delivery systems in the skincare treatments disclosed herein. Such masks may be shaped to be attached to, for example, the face and may be made of non-woven fabrics, such as vegetable cellulose fibers, i.e., cotton or pulp, or of synthetic fibers.

In certain embodiments disclosed herein, biocellulose sheets pre-moistened, i.e., saturated, with formulations disclosed herein may be used for applying to the skin. The present disclosure provides biocellulose face masks that are manufactured using biocellulose sheets. The sheets are shaped to, for example, facial contours. The formed masks are then impregnated, i.e., moistened, with the skincare formulations disclosed herein. The pre-moistened masks are then packed in, for example, foil pouches and irradiated for sterilization. Laboratory testing is conducted to ensure mask quality standards.

Formulations of the present disclosure may be prepared under ambient conditions. In certain embodiments, formulations of the present disclosure are prepared under an inert atmosphere. In particular aspect of this embodiment, the inert atmosphere is an inert gas, such as but not limited to, nitrogen, argon, or combinations thereof. In certain embodiments formulations of the present disclosure are prepared under a dry inert atmosphere, which may comprise, consist essentially of, or consist of one or more dry inert gases, including but not limited to dry nitrogen, dry argon, or a combination thereof.

EXAMPLE

Dermatologic procedures may be accompanied by slow healing and post-treatment discomfort. Biocellulose masks according to the present disclosure are designed to, for example, relieve post-procedure discomfort, improve rates of healing, and reduce the appearance of redness, among other beneficial results disclosed herein.

The following study was carried out to evaluate the efficacy and safety of a sterile, treatment-formulation infused, biocellulose mask according to the present disclosure to accelerate healing, enhance improvement, and reduce post-procedure discomfort following a RF/microneedling treatment of the face.

Ten healthy females aged 35 to 60 years, moderate wrinkles, enrolled in the open-label, single-site pilot study. Subjects were treated once with 2 passes of a microneedle radio-frequency (RF) device. Treatment was immediately followed by application of a biocellulose mask according to the present disclosure to the entire face for 15 to 20 minutes. Subjects were given an additional six masks for daily home use and asked to return to the office 3 and 7 days later for evaluation of efficacy and safety. Skin responses were tracked by photography of subjects' faces immediately post-procedure (pre- and post-mask application), and on days 3 and 7. Clinical grading was performed.

Subjects achieved statistically significant improvement in skin radiance, smoothness, texture, and dryness after a single RF/microneedling treatment followed by daily usage of the biocellulose mask for 1 week. Skin tone evenness, red/blotchiness, and overall appearance were trending toward significant improvement by Day 7. Adverse events were not observed in any subject.

The results demonstrate the effectiveness of the disclosed biocellulose masks pre-moistened with the disclosed formulations in soothing skin and accelerating its healing post a RF/microneedling procedure. The masks and formulations according to the present disclosure may be used directly on compromised skin immediately post-microneedling, without any adverse events. Improvement and conditioning of the facial skin using the disclosed masks daily for one week after treatment has been shown.

| Exemplary Composition Ranges | | |
| --- | --- | --- |
| Ingredient | %(w/w) | %(w/w) |
| Purified Water | QS to 100% | 82.41% |
| Disodium EDTA | 0.02 | 0.05% |
| Caffeine | 1.00 | 0.01% |
| Sodium Benzoate | 0.1 | 0.05% |
| Hydrolyzed Sodium Hyaluronate | 2.0 | 1.00% |
| Sodium Hyaluronate | 0.5 | 0.10% |
| *Cucumis Sativus* (Cucumber) Fruit Extract | 10.0 | 0.01% |
| *Camellia Sinensis* Leaf Extract | 10.0 | 0.01% |
| Ecto in | 0.2 | 0.01% |
| Ergothioneine | 0.1 | 0.01% |
| *Yucca Glauca* Root Extract | 10.0 | 0.01% |
| Sodium PCA | 5.0 | 0.01% |
| *Chamomilla Recutita* (*Matricaria*) Flower Extract | 5.0 | 0.01% |
| ABS Comfrey Extract PF: *Symphytum Officinale* Leaf Extract, *Leuconostoc*/Radish Root Ferment Filtrate | 2.0 0.05 | 0.01% |
| *Phyllanthus Emblica* Fruit Extract | 0.25 | 0.10% |

-continued

Exemplary Composition Ranges

| Ingredient | %(w/w) | %(w/w) |
|---|---|---|
| Purified Water | 0.9 | 10.00% |
| Polysorbate 20 | 2.2 | 0.70% |
| Phenylcarbinol | 0.95 | 0.20% |
| Bisabolol | 1.5 | 0.20% |
| Resveratrol | 0.75 | 0.01% |
| Palmitoyl sh-Tripeptide Amide solution | 10.0% | 4.00% |
| Sodium Phosphate | 0.55 | 0.638% |
| Potassium Hydroxide | 0.20 | 0.226% |
| Purified Water | 1.0 | 0.226% |

What is claimed is:

1. A topical formulation for therapeutic treatment of skin in dermatological procedures, comprising (% w/w)
0.001%-10% sodium hyaluronate,
an oligopeptide, wherein the oligopeptide is 0.0001%-10% palmitoyl sh-tripeptide-4 amide on an active basis,
one or more antioxidants, wherein the one or more antioxidants is between 0.1%-10% w/w and comprises one or more of *Camellia sinensis* leaf extract, resveratrol, ectoin, *Cucumis satvius* fruit extract, ergothioneine, *Phyllanthus emblica* fruit extract,
10%-99% purified water;
0.001%-75% hydrolyzed sodium hyaluronate;
0.001%-99% *Camellia sinensis* leaf extract;
0.001%-5.0% resveratrol;
0.001%-5% ectoin;
0.001%-5% ergothioneine;
0.001%-5% bisabolol;
0.001%-99% *Cucumis* satvius fruit extract;
0.001%-99% sodium pyrrolidone carboxylic acid (PCA);
0.001%-99% *Chamomila recutita* flower extract;
0.001%-99% comfrey extract;
0.001%-99% *yucca glauca* root extract;
0.001%-5% *Phyllanthus emblica* fruit extract;
0.001%-5% caffeine;
0%-2% sodium phosphate;
0%-0.5% potassium hydroxide;
0.0%-3.5% phenylcarbinol;
0.0%-0.5% sodium benzoate;
0.0%-0.3% disodium Ethylenediaminetetraacetic acid (EDTA); and
0.01%-10% polysorbate 20.

2. The formulation of claim 1, comprising (% w/w):
82.41% purified water;
1.00% hydrolyzed sodium hyaluronate;
0.10% sodium hyaluronate;
0.01% *Camellia sinensis* leaf extract;
0.01% resveratrol;
4.00% palmitoyl sh-tripeptide-4 amide;
0.01% ectoin;
0.01% ergothioneine;
0.20% bisabolol;
0.01% *Cucumis satvius* fruit extract;
0.01% sodium pyrrolidone carboxylic acid (PCA);
0.01% *Chamomila recutita* flower extract;
0.01% comfrey extract (*Symphytum officinale* leaf extract, *Leuconostoc*/radish root ferment filtrate);
0.01% *yucca glauca* root extract;
0.10% *Phyllanthus emblica* fruit extract;
0.01% caffeine;
0.638% sodium phosphate;
0.226% potassium hydroxide;
0.20% phenylcarbinol;
0.05% sodium benzoate;
0.05% disodium Ethylenediaminetetraacetic acid (EDTA); and
0.70% polysorbate 20.

3. A sheet for therapeutic treatment of skin in dermatological procedures, comprising the sheet structured for topical application to skin selected for a dermatological procedure, the sheet being pre-moistened with a therapeutically effective amount of a formulation of claim 1.

4. The sheet of claim 3, wherein the sheet is a biocellulose sheet and is structured as a facial mask.

5. The sheet of claim 3, wherein the formulation and/or sheet pre-moistened with the formulation is sterilized.

6. The topical formulation of claim 1, wherein the formulation is sterile.

7. The topical formulation of claim 1, wherein the formulation is a sheet.

* * * * *